(12) United States Patent
Kraft

(10) Patent No.: US 6,723,313 B2
(45) Date of Patent: Apr. 20, 2004

(54) 2-,5-,6-,7-,8-SUBSTITUTED OCT-2-EN-4-ONES

(75) Inventor: Philip Kraft, Dübendorf (CH)

(73) Assignee: Givaudan SA, Geneve (CH)

( * ) Notice: Subject to any disclaimer, the term of this patent is extended or adjusted under 35 U.S.C. 154(b) by 0 days.

(21) Appl. No.: 09/844,805

(22) Filed: Apr. 27, 2001

(65) Prior Publication Data

US 2002/0176838 A1 Nov. 28, 2002

(30) Foreign Application Priority Data

Apr. 28, 2000 (CH) .................................... 2000 0850100

(51) Int. Cl.⁷ ................................................. A61L 9/00
(52) U.S. Cl. ....................... 424/76.1; 568/303; 424/76.4
(58) Field of Search .............................. 424/76.1, 76.4; 568/303

(56) References Cited

U.S. PATENT DOCUMENTS

| 4,380,674 A | 4/1983 | Boden |
| 4,448,713 A | 5/1984 | Boden |

FOREIGN PATENT DOCUMENTS

| EP | 141 569 | 5/1985 |
| JP | 55027135 | * 2/1980 |

OTHER PUBLICATIONS

Kibina et al Reactions of acetylenic 1,2,5–triols in an acidic medium Deposited Doc VINITI 1982.*
D. Kastner, *Perfume, Kosmet.*, 66, 5–16 (1985).
D. Kastner, *Perfume, Kosmet.*, 75, 170–181 (1994).
G. Ohloff, *J. Chromatogr.*, 406, 181–183 (1987).
M. Gras, *Perfum. Flavor*, 15, 25–28 (1990).
M. Gras, *Perfum. Flavor*, 17, 1–12 (1992).
G. Frater, *Tetrahedron*, 54, 7633–7703 (1998).
H. Vieregge, *Recl. Trav. Chim, Pays–Bas*, 85(9–10), 929–951 (1966).
Kraft et al. "5,6,7–Trimethylocta–2,5–dien–4–one—A Suspected Odorant with Surprising Olfactory Properties", Eur. J. Org. Chem. 2001, 2363–2369.
Kibina, I., et al., *Chemical Abstracts*, v. 100 (13); 102702f (1984).

* cited by examiner

*Primary Examiner*—Thurman K. Page
*Assistant Examiner*—Lakshmi Channavajjala
(74) *Attorney, Agent, or Firm*—Norris McLaughlin & Marcus, PA

(57) ABSTRACT

The invention relates to 2-,5-,6-,7-,8-substituted oct-2-en-4-ones, to a process for delivering these compounds as a fragrance, an aroma, or a flavoring, and to fragrance and aroma compositions prepared therewith.

19 Claims, No Drawings

2-,5-,6-,7-,8-SUBSTITUTED OCT-2-EN-4-ONES

FIELD OF THE INVENTION

The invention relates to 2-,5-,6-,7-,8-substituted oct-2-en-4-ones, to a process of using these compounds as a fragrance, an aroma, or a flavoring, and to fragrance or aroma compositions prepared therewith.

BACKGROUND OF THE INVENTION

Until the discovery of the 1-(2,2,6-trimethylcyclohexyl) but-2-en-1-ones, called damascones, a perfumistic reconstitution of rose oil was virtually impossible (D. Kastner, *Parfuem. Kosmet.* 1985, 66, 5–16; D. Kastner, *Parfuem. Kosmet.* 1994, 75, 170–181). With the discovery of the damascones (G. Ohloff, E. Demole, *J. Chromatogr.* 1987, 406, 181–183), however, not only did this change, but the substance class also gave many other floral or fruity accords volume, freshness and naturalness. Moreover, excessive amounts set entirely new trends (M. Gras, *Perfum. Flavor.* 1990, 15, 25–28; M. Gras, *Perfum. Flavor.* 1992, 17, 1–12). There have been many attempts to find substances with similar odor properties, some of which have become established in perfumery (G. Fráter, J. A. Bajgrowicz, P. Kraft, *Tetrahedron* 1998, 54, 7633–7703). However, these compounds are structurally very similar to the damascones and, apart from a few exceptions, are constitutionally isomeric thereto. In addition, the Japanese laid-open specification JP 55027135 discloses 3(4),4(5)-diseco- and 2(3),4(5)-diseco-damascones. From a perfumery viewpoint, all of these compounds offer very little which is new, i.e. they broaden the odor spectrum around the parent compounds only insignificantly, and thus do not satisfy the need for novel innovative scent building-blocks of this odor direction.

As a result of the structural similarities and the similar molecular weight, the known compounds having damascone-like odor properties established in perfumery have very similar application properties, i.e. a comparable diffusivity, substantivity, and radiative power in compositions. They do not, in fact, satisfy the need for innovative, novel scent building-blocks with other areas of application.

SUMMARY OF THE INVENTION

An object of the invention is to rectify this deficit and to extend the odiferous spectrum of the damascones by novel facets in order to open up new composition possibilities for the perfumer and flavorist.

Accordingly, it would be advantageous to provide a group of branched acyclic alkenones of the general formula I:

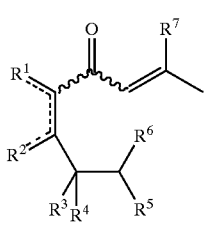

in which
$R^1$ and $R^2$ are independently $CH_2$, $CH_3$, $CHCH_3$, or $CH_2CH_3$;
$R^3$ is H, $CH_3$, or $CH_2CH_3$; and
$R^4$, $R^5$, $R^6$, $R^7$ are independently H or $CH_3$, with the proviso that the radicals $R^4$, $R^5$, $R^6$, and $R^7$ are not all hydrogen at the same time, and where the dashed line represents an optional double bond. This new group of compounds enriches the typical odor properties of the damascones with novel, characteristic aspects. Such compounds have completely different application properties, primarily with regard to a much greater diffusivity and radiative power. Some of these compounds are also much more odor-intensive than the damascones themselves.

Another embodiment of the present invention is a process for preparing a fragrance, a flavor, or an aroma composition wherein a base material is combined with a compound of the general formula I:

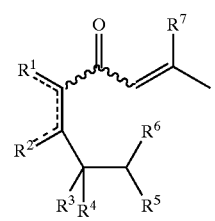

wherein
$R^1$ and $R^2$ independently are $CH_2$, $CH_3$, $CHCH_3$, or $CH_2CH_3$;
$R^3$ is H, $CH_3$, or $CH_2CH_3$;
$R^4$, $R^5$, $R^6$, and $R^7$ independently are H or $CH_3$; with the proviso that $R^4$, $R^5$, $R^6$, and $R^7$ are not all hydrogen, and where the dashed line represents an optional double bond.

A further embodiment of the present invention is a process for delivering a fragrance, flavor, or aroma to a substrate by contacting a substrate with a fragrance, flavor, or aroma composition comprising a base material and a compound of formula I:

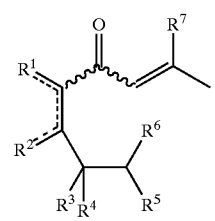

wherein
$R^1$ and $R^2$ independently are $CH_2$, $CH_3$, $CHCH_3$, or $CH_2CH_3$;
$R^3$ is H, $CH_3$, or $CH_2CH_3$;
$R^4$, $R^5$, $R^6$, and $R^7$ independently are H or $CH_3$; with the proviso that $R^4$, $R^5$, $R^6$, and $R^7$ are not all hydrogen, and where the dashed line represents an optional double bond.

DETAILED DESCRIPTION OF THE INVENTION

The present invention provides 2-,5-,6-,7-,8-substituted oct-2-en-4-ones according to formula I:

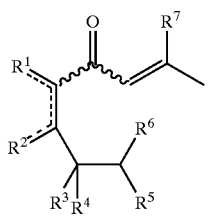

I wherein
- $R^1$ and $R^2$ independently are $CH_2$, $CH_3$, $CHCH_3$, or $CH_2CH_3$;
- $R^3$ is H, $CH_3$, or $CH_2CH_3$;
- $R^4$, $R^5$, $R^6$, and $R^7$ independently are H or $CH_3$; with the proviso that $R^4$, $R^5$, $R^6$, and $R^7$ are not all hydrogen, and where the dashed line represents an optional double bond.

According to the general formula I, a double bond does not have to be present at positions $R^1$(C-5), C-5(C-6), and $R^2$(C-6). (E/Z)-Isomers of all double bonds (at most two) present in a molecule and all possible stereoisomers are covered by the general formula I, which is shown in the formula by waved lines.

The compounds according to the invention are therefore characterized by an oct-2-en-4-one skeleton. Due to the specific odor and/or aroma properties, compounds with a 7-methyloct-2-en-4-one skeleton are preferred, and compounds with a (5Z)-7-methylocta-2,5-dien-4-one skeleton are particularly preferred.

The general formula I thus covers the compounds 1–9:

1

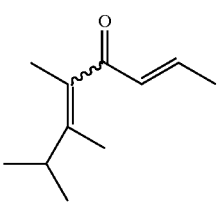

2

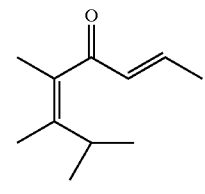

3

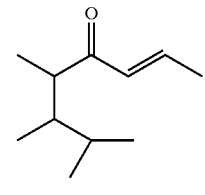

4

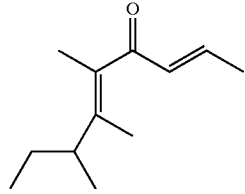

5

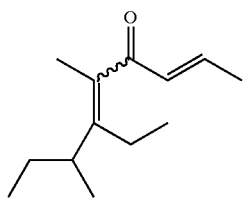

6

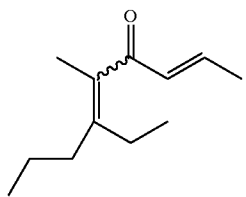

7

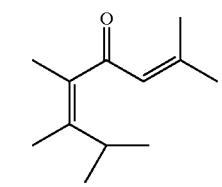

8

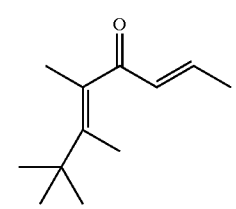

9

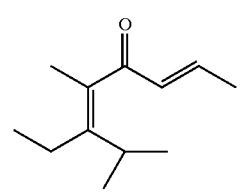

The compounds of the general formula I are particularly suitable for the composition of rosy accords, and generally floral bouquets. Particular mention is to be made also of the use in fruity notes and musk-accentuated compositions. However, the use is neither limited to these accords, nor to specific fragrances, classes of substance, or odor notes. Examples of further classes of substances which harmonize well with the compounds of the present invention and that may be combined therewith include:

| | |
|---|---|
| Essential oils and extracts, e.g. | ambrette resinoid, bergamot oil, geranium oil, grapefruit oil, mandarin oil, patchouli oil, rose absolute, sandalwood oil, ylang-ylang oil, lemon oil. |
| Alkanes, alkenes, halogen compounds, e.g. | farnesene, alpha-trichloromethylbenzyl acetate. |
| Alcohols, ethers, acetals, e.g. | citronellol, dihydromyrcenol, Ebanol ®, eugenol, Florol ®, geraniol, Helional ®, cis-hex-3-enol, Mayol ®, nerol, 2-phenylethyl alcohol, rose oxide, Sandalore ®, Spirambrene ®. |
| Aldehydes and ketones, e.g. | Adoxal ®, Bourgeonal ®, cepionate, Cyclohexal ®, damascenone, beta-dihydroionone, Florhydral ®, Hedione ®, raspberry ketone (N-112), hydroxycitronellal, Iso E Super ®, Lemarom ®, Lilial ®, methylionone, 2-methylundecanal, Myraldene ®, 10-undecen-1-al, undecanal, vanillin, Vertofix ®. |
| Esters, lactones, nitriles, e.g. | Allyl amyl glycolate, benzyl salicylate, citronellyl acetate, citronellyl formate, Cyclogalbanate ®, decalactone gamma, Gardenol ®, geranyl acetate, cis-hex-3-enyl acetate, hexyl acetate, linalyl acetate, phenylethyl acetate, Peonile ®, gamma-undecalactone, Verdox ®. |
| Macro-, poly-, heterocycles, e.g. | Ambroxan ®, Cashmeran ®, Galaxolide ®, Habanolide ®, Thibetolide ®. |

The compounds of the present invention may be combined, alone or in combination, with a base material to form a fragrance, a flavor, or an aroma composition. As used herein, a "fragrance, a flavor, or an aroma composition" includes perfumes, detergents, soaps, creams, shampoos, hair conditioners, food stuffs (including gum), beverages, and food. As used herein, a "base material" includes any standard formulation conventionally found in a fragrance, a flavor, or an aroma composition as defined above. Examples of typical base materials are set forth in Examples 10 and 11.

The present invention also includes a process for providing a fragrance or aroma. This process includes combining one or more compounds according to formula I with a base material to form the fragrance or aroma composition. The fragrance or aroma composition is then applied to a substrate or liberated, in the case of a candle by burning. As used herein, a "substrate" means a surface to which a fragrance or aroma composition is typically applied. Thus, for example, a substrate may be human skin in the case of a perfume, soap, or cream; hair in the case of a shampoo, mousse, or gel; a fabric in the case of a detergent or fabric softener; or a hard surface in the case of a cleaning agent.

The following examples are provided to further illustrate the compounds, compositions, and processes of the present invention. These examples are illustrative only and are not intended to limit the scope of the invention in any way.

EXAMPLES

Example 1

(2E,5E/Z)-5,6,7-Trimethylocta-2,5-dien-4-one (1)

Ethyl (2E/Z)-2,3,4-trimethylpent-2-enoate was prepared in accordance with the procedure of H. Vieregge, H. M. Schmidt, J. Renema, H. J. T. Bos and J. F. Arends (*Recl. Trav. Chim. Pays-Bas* 1966, 85(9–10), 929–951) in 58 percent yield by boron-trifluoride-catalyzed addition of methyl isopropyl ketone to 1-ethoxypropyne. The portionwise addition of a solution of 6.3 ml (73.9 mmol) of 1-bromoprop-1-ene in 60 ml of dry tetrahydrofuran to 1.80 g (73.9 mmol) of magnesium turnings with sporadic heating using a hot-air pistol under an inert-gas atmosphere gave a Grignard solution. In a further reaction vessel, a lithium diisopropylamide solution was prepared under nitrogen at −70° C. by the dropwise addition of 4.3 ml (42.7 mmol) of 10 M butyllithium solution to a solution of 6.1 ml (42.7 mmol) of diisopropylamine in 22 ml of dry tetrahydrofuran and subsequent stirring for 10 minutes at this temperature. Then, at room temperature over the course of 20 minutes, the previously prepared Grignard solution was added dropwise, followed, at 35° C., again over the course of 20 minutes, by a solution of ethyl (2E/Z)-2,3,4-trimethylpent-2-enoate dissolved in 90 ml of dry tetrahydrofuran. After the mixture had been stirred for 2 hours at 35° C. and heated under reflux for 1 hour, it was poured onto water, and the product was extracted with ether. The combined ether extracts were washed with water and saturated sodium chloride solution, dried over sodium sulfate and evaporated on a rotary evaporator. Flash chromatography (pentane/ether, 19:1, $R_f$=0.22) gave 1.8 g (25%) of (2E,5E/Z)-5,6,7-trimethylocta-2,5-dien-4-one (1) as a colorless liquid with a characteristic odor.

Odor: linear, very intensive and very diffusive, fruity-rosy, resembling dried apples, plums, raisins, and other dried fruit; in the top note slightly rum- and caramel-like. -IR (film): ν=1653 cm$^{-1}$ (νC=O, unsat.), 1620 (νC=C), 973 (δC=C—H oop.), 1377 (δCH$_3$). -$^1$H-NMR (CDCl$_3$): δ=0.94 (d, J=6.6 Hz, 6H, 7-Me$_2$, 5E), 1.01 (d, J=6.8 Hz, 6H, 7-Me$_2$, 5Z), 1.54 (q, $^5$J=1.3 Hz, 3H, 6-Me, 2E, 5Z), 1.61 (q, $^5$J=0.97 Hz, 3H, 6-Me, 2E, 5E), 1.74 (q, $^5$J=0.97 Hz, 3H, 5-Me, 2E, 5E), 1.79 (q, $^5$J=1.3 Hz, 3H, 5-Me, 2E, 5Z), 1.91–1.94 (m, 6H, 1-H$_3$, 5E+5Z), 2.57 (sept, J=6.6 Hz, 1H, 7-H, 5E), 2.86 (sept, J=6.8 Hz, 1H, 7-H, 5Z), 6.11 (dq, J=15.9, 2.0 Hz, 1H, 3-H, 2E, 5Z), 6.12 (dq, J=15.6, 1.6 Hz, 1H, 3-H, 2E, 5E), 6.74 (dq, J=15.9, 9.2 Hz, 1H, 2-H, 2E, 5Z), 6.77 (dq, J=15.6, 6.8 Hz, 1H, 2-H, 2E, 5E). -$^{13}$C-NMR (CDCl$_3$): δ=11.21/13.77 (2q, 5-Me), 15.02/15.91 (2q, 6-Me), 18.10/18.21 (2q, C-1), 19.97/20.39 (4q, 7-Me$_2$), 29.52/32.35 (2d, C-7), 128.69/128.81 (2s, C-5), 132.03/132.41 (2d, C-3), 140.32/140.47 (2s, C-6), 145.11/145.32 (2d, C-2), 201.57/201.77 (2s, C-4). -MS (EI): m/e (%)=41 (43) [C$_3$H$_5$], 55 (30) [C$_4$H$_7$], 69 (32) [C$_4$H$_5$O], 123 (20) [M$^+$-C$_3$H$_7$], 136 (31) [M$^+$-2CH$_3$], 151 (100) [M$^+$-CH$_3$], 166 (11) [M$^+$].

Example 2

(2E,5Z)-5,6,7-Trimethylocta-2,5-dien-4-one (2)

Using flash chromatography (pentane/ether, 9:1, R$_f$=0.53) of the (2E,5E/Z) mixture 1, it was possible to isolate a sample of uniformly (2E,5Z)-configured 5,6,7-trimethylocta-2,5-dien-4-one (2) as a colorless liquid having an extremely intensive odor which exhibited the following olfactory and spectroscopic data.

Odor: Corresponds to compound 1, but is much more intensive and radiative; threshold value: 0.5 ng/l of air whereas the (5E)-isomer shows a threshold value of 500 ng/l. -IR (film): ν=1653 cm$^{-1}$ (νC=O, unsat.), 1620 (νC=C), 973 (δC=C—H oop.), 1377 (δCH$_3$). -$^1$H-NMR (CDCl$_3$): δ=0.94 (d, J=6.6 Hz, 6H, 7-Me$_2$), 1.61 (q, $^5$J=1.0 Hz, 3H, 6-Me, hence 5Z, the 5E-isomer is at 1.5 Hz), 1.74 (q, $^5$J=1.0 Hz, 3H, 5-Me, hence 5Z, the 5E-isomer is at 1.5 Hz), 1.92 (dd, J=6.8, 1.6 Hz, 3H, 1-H$_3$), 2.57 (sept, J=6.6 Hz, 1H, 7-H), 6.12 (dq, J=15.6, 1.6 Hz, 1H, 3-H, hence 2E), 6.77 (dq, J=15.6, 6.8 Hz, 1H, 2-H, hence 2E). -NOESY ($^1$H/$^1$H): 3-H/7-Me, 5-Me/6-Me. -$^{13}$C-NMR (CDCl$_3$): δ=11.29 (q, 5-Me), 15.99 (q, 6-Me), 18.18 (q, C-1), 20.45 (2q, 7-Me$_2$), 32.41 (d, C-7), 128.85 (s, C-5), 132.47 (d, C-3), 140.45 (s, C-6), 145.41 (d, C-2), 201.94 (s, C-4). -MS (EI): m/e (%)=41 (41) [C$_3$H$_5$], 55 (30) [C$_4$H$_7$], 69 (31) [C$_4$H$_5$O], 123 (20) [M$^+$-C$_3$H$_7$], 136 (33) [M$^+$-2CH$_3$], 151 (100) [M$^+$-CH$_3$], 166 (11) [M$^+$].

Example 3

(2E)-5,6,7-Trimethyloct-2-en-4-one (3)

20.0 g (117 mmol) of a double-bond isomer mixture of ethyl 2,3,4-trimethylpent-2-enoate (synthesis: see example 1) were dissolved in 200 ml of ethyl acetate, treated with 0.50 g (0.26 mmol, 0.2 mol %) of 10 percent platinum on activated carbon, and hydrogenated at room temperature for 4 hours in an autoclave at a hydrogen atmosphere of 25 bar with vigorous stirring. The catalyst was separated off by filtering the reaction mixture with suction over Celite. After the solvent had been removed on a rotary evaporator, the mixture was distilled under reduced pressure over a 10 cm Widmer column, giving 16.9 g (83%) of colorless ethyl 2,3,4-trimethylvalerate at a boiling point of 105–108° C./100 mbar. These 16.9 g (98.1 mmol) were dissolved in 150 ml of ethanol/water (1:1) and 9.60 g (147 mmol) of 86 percent potassium hydroxide were added. The reaction mixture was refluxed for 2 hours and, after cooling, diluted with 500 ml of water and adjusted to pH 1 with hydrochloric acid. The aqueous phase was extracted three times with ether, and the combined organic phases were dried over sodium sulfate and evaporated on a rotary evaporator. This gave 14.3 g of crude 2,3,4-trimethylvaleric acid which was dissolved in 250 ml of dry tetrahydrofuran. At −10° C., 9.8 ml (98 mmol) of 10 M butyllithium solution in hexane were added dropwise. After the mixture had been stirred for 40 minutes at −10° C., 123 ml (98 mmol) of 0.8 M propenyllithium solution in ether were slowly added dropwise at this temperature. After stirring for 4 hours at 30° C., the mixture was cooled to −10° C., and 16 ml (218 mmol) of acetone were added dropwise at this temperature. After the mixture had been stirred for a further 10 minutes at −10° C., 200 ml of saturated ammonium chloride solution were added dropwise at this temperature. The cooling was removed and the reaction mixture was diluted with 200 ml of water. The aqueous phase was extracted three times with ether, and the combined organic extracts were dried over magnesium sulfate and evaporated on a rotary evaporator. Flash chromatography (pentane/ether, 19:1, R$_f$=0.24) over silica gel gave 6.50 g (39%) of (2E)-5,6,7-trimethyloct-2-en-4-one as a colorless liquid with a pleasant odor.

Odor: Weaker than 1 and 2, but also very diffusive, fruity-rosy, reminiscent of raspberries and dried fruits. -IR (film): ν=1629 cm$^{-1}$ (νC=C), 1695/1668 (νC=O, unsat.), 970 (δC=C—H oop.), 1378 (δCH$_3$). -$^1$H-NMR (CDCl$_3$): δ=0.70/0.74/0.76/0.84 (4d, J=6.8 Hz, 6H, 7-Me$_2$), 0.92/0.93 (2d, J=6.5 Hz, 3H, 6-Me), 0.98/1.05 (2d, J=6.8 Hz, 3H, 5-Me), 1.49–1.71 (m, 1H, 7-H), 1.85–1.93 (m, 4H, 1-H$_3$, 6-H), 2.78 (quint, J=6.8 Hz)/2.61 (dq, J=9.6, 6.8 Hz) [1H, 5-H], 6.21 (dq, J=15.4, 1.6 Hz, 1H, 3-H), 6.85–6.94 (m, 1H, 2-H). -$^{13}$C-NMR (CDCl$_3$): δ=11.03/11.69 (4q, 7-Me$_2$), 14.97/15.19 (2q, 5-Me), 18.08/18.22 (2q, C-1), 21.35/21.42 (2q, 6-Me), 27.10/30.30 (2d, C-7), 40.33/40.50 (2d, C-6), 46.73/47.70 (2d, C-5), 130.19/130.87 (2d, C-3), 141.83/142.19 (2d, C-2), 203.83/204.47 (2s, C-4). -MS (EI): m/e (%)=69 (100) [C$_4$H$_5$O$^+$], 83 (16) [M$^+$-C$_5$H$_{10}$-CH$_3$], 98 (58) [M$^+$-C$_5$H$_{10}$, McLafferty fragmentation], 125 (2) [M$^+$-C$_3$H$_7$], 168 (1) [M$^+$].

Example 4

(2E,5E)-5,6,7-Trimethylnona-2,5-dien-4-one (4)

Using the procedure of example 1 and the general procedure of H. Vieregge, H. M. Schmidt, J. Renema, H. J. T. Bos and J. F. Arends (Recl. Trav. Chim. Pays-Bas 1966, 85(9–10), 929–951], ethyl 2,3,4-trimethylhex-2-enoate was prepared by the addition of 3-methylpentan-2-one to 1-ethoxypropyne in 46 percent yield. 5.83 g (31.7 mmol) of this ethyl 2,3,4-trimethylhex-2-enoate were dissolved in 100 ml of ethanol/water (1:1) and then 2.93 g (44.4 mmol) of 86 percent strength potassium hydroxide were added. After the mixture had been refluxed for 3 hours, a further 2.93 g (44.4 mmol) of 86 percent strength potassium hydroxide were added, and the reaction mixture was then refluxed for a further 3 hours. After cooling, 300 ml of water were added and the mixture was acidified with concentrated phosphoric acid. The aqueous phase was extracted with 400 ml of ether, and the organic phases were dried and evaporated to dryness on a rotary evaporator. After flash chromatography (pentane/ether, 4:1) over silica gel, 3.77 g (76%) of 2,3,4-trimethylhex-2-enoic acid were isolated, which were taken up in 50 ml of dry tetrahydrofuran. At −10° C., 15.1 ml (24.2 mmol) of 1.6 M butyllithium solution in tetrahydrofuran were added dropwise under nitrogen. After the mixture had been stirred for 15 minutes at this temperature, 30.0 ml (24.2 mmol) of propenyllithium solution in ether were added dropwise over the course of 10 minutes. The cooling was removed and the reaction mixture was heated to 30° C. It was stirred for 1 hour at this temperature, then cooled to 0° C., and 4 ml of acetone, followed by 50 ml of saturated ammonium chloride solution, were added dropwise. After the reaction mixture had been heated to room temperature, it was diluted with 200 ml of water, and the product was extracted by washing three times with 400 ml of ether. The organic extracts were combined, dried and evaporated on a rotary evaporator, and the crude product was subjected to flash chromatography over silica gel with 4 l of pentane/ether (49:1) and 2 l of pentane/ether (19:1). As a result, 0.67 g (15%) of (2E,5E)-5,6,7-trimethylnona-2,5-dien-4-one (4) was isolated as a colorless liquid having an intensive and characteristic odor.

Odor: Linear, very intensive, and long-lasting, fruity-rosy, reminiscent of apples and dried fruit. -IR (film): $\nu$=1652 cm$^{-1}$ ($\nu$C=O, unsat.), 972 ($\delta$C=C—H oop.), 1620 ($\nu$C=C), 1376 ($\delta$CH$_3$). -$^1$H-NMR (CDCl$_3$): $\delta$=0.87 (t, J=7.4 Hz, 3H, 9-H$_3$), 0.99 (d, J=7.2 Hz, 3H, 7-Me), 1.38 (qd, J=7.4, 7.2 Hz, 2H, 8-H$_2$), 1.50 (q, $^5$J=1.5 Hz, 3H, 6-Me), 1.79 (q, $^5$J=1.5 Hz, 3H, 5E-Me), 1.92 (dd, J=6.8, 1.6 Hz, 3H, 1-H$_3$), 2.60 (sext, J=7.2 Hz, 1H, 7-H), 6.11 (dq, J=15.6, 1.6 Hz, 1H, 3-H), 6.80 (dq, J=15.6, 6.8 Hz, 1H, 2E-H). -$^{13}$C-NMR (CDCl$_3$): $\delta$=12.17 (q, C-9), 13.63 (q, 5-Me), 15.35 (q, 6-Me), 18.16/18.23 (2q, C-1, 7-Me), 27.26 (t, C-8), 36.74 (d, C-7), 130.09 (s, C-5), 132.14 (d, C-3), 139.09 (s, C-6), 145.06 (d, C-2), 201.77 (s, C-4). -MS (EI): m/e (%)=41 (73) [C$_3$H$_5$], 55 (33) [C$_4$H$_7$], 69 (62) [C$_4$H$_5$O], 109 (43) [M$^+$-C$_5$H$_{11}$], 123 (43) [M$^+$-C$_4$H$_9$], 136 (17) [M$^+$-C$_3$H$_8$], 151 (100) [M$^+$-C$_2$H$_5$], 165 (26) [M$^+$-CH$_3$], 180 (13) [M$^+$].

Example 5

(2E,5E/Z)-6-Ethyl-5,7-dimethylnona-2,5-dien-4-one (5)

Using the procedure of example 4,3-ethyl-2,4-dimethylhex-2-enoic acid was prepared from ethoxypropyne and 4-methylhexan-3-one. 0.60 g (3.52 mmol) of 3-ethyl-2,4-dimethylhex-2-enoic acid was initially introduced into 10 ml of dry tetrahydrofuran at −10° C. At this temperature, 0.35 ml (3.5 mmol) of 10M butyllithium solution was slowly injected using a syringe over the course of 15 minutes, and, after stirring for a further 45 minutes, 3.52 ml (3.52 mmol) of 1M propenyllithium solution in ether were added and the mixture was stirred for 15 hours at room temperature. It was then cooled again to −10° C., and the reaction mixture was treated at this temperature with 0.6 ml of acetone and, after stirring for 10 minutes, with 7 ml of saturated ammonium chloride solution. The reaction mixture was then poured onto 50 ml of water, and the product was extracted with 2 ×50 ml of ether. The extracts were combined, washed in each case with 50 ml of water and 25 ml of saturated sodium chloride solution, dried over sodium sulfate and evaporated to dryness on a rotary evaporator. After flash chromatography (pentane/ether, 98:2, R$_f$=0.37) on silica gel, 200 mg (29%) of colorless (2E,5E/Z)-6-ethyl-5,7-dimethylnona-2,5-dien-4-one (5) with a pleasant odor were isolated.

Odor: Fruity-rosy, reminiscent of dried fruits, but with a significant caramel- and icing-like nuance. -IR (film): $\nu$=1652 cm$^{-1}$ ($\nu$C=O, unsat.), 973 ($\delta$C=C—H oop.), 1623 ($\nu$C=C), 1376 ($\delta$CH$_3$). -$^1$H-NMR (CDCl$_3$): $\delta$=0.76/0.90 (t, J=7.4 Hz, 3H, 9-H$_3$), 0.95/0.96 (2t, J=7.2 Hz, 3H, CH$_3$, 6-Et), 1.06/1.08 (2d, J=7.2 Hz, 3H, 7-Me), 1.26–1.50 (m, 2H, 8-H$_2$), 1.78/1.79 (2br. s, 3H, 5-Me), 1.91/1.93 (2t, J=1.6 Hz, 3H, 1-H$_3$), 1.98/2.05 (2br. q, J=7.2 Hz, 2H, CH$_2$, 6-Et), 2.24/2.55 (sext, J=7.1 Hz, 1H, 7-H), 6.10/6.12 (2dq, J=15.6, 1.6 Hz, 1H, 3-H), 6.78 (br. dq, J=15.6, 6.8 Hz, 1H, 2E-H). -$^{13}$C-NMR (CDCl$_3$): $\delta$=12.22/12.48 (2q, C-9), 13.95/15.25 (2q, 5-Me), 15.73/15.79 (2q, CH$_3$, 6-Et), 18.12/18.18/18.64/18.77 (4q, C-1, 7-Me), 19.50/22.35 (2t, CH$_2$, 6-Et), 27.72/27.96 (2t, C-8), 37.49/40.24 (2d, C-7), 130.69 (2s, C-5), 132.08/132.64 (2d, C-3), 144.51/144.80 (2s, C-6), 144.91/145.17 (2d, C-2), 201.66/202.11 (2s, C-4). -MS (EI): m/e (%)=41 (65) [C$_3$H$_5$], 55 (28) [C$_4$H$_7$], 69 (49) [C$_4$H$_5$O], 123 (35) [M$^+$-C$_5$H$_{11}$], 137 (76) [M$^+$-C$_4$H$_9$], 165 (100) [M$^+$-C$_2$H$_5$], 179 (25) [M$^+$-CH$_3$], 194 (5) [M$^+$].

The compounds set forth in examples 6–9 were prepared using the processes of examples 1–5 as required. For these, therefore, only the olfactory characterization and the spectroscopic data are listed.

Example 6

(2E,5E/Z)-6-Ethyl-5-methylnona-2,5-dien-4-one (6)

Odor: Fruity-rosy, reminiscent of dried fruits, with a slightly green hint. -IR (film): $\nu$=1652 cm$^{-1}$ ($\nu$C=O, unsat.), 972 ($\delta$C=C—H oop.), 1376 ($\delta$CH$_3$). -$^1$H-NMR (CDCl$_3$): $\delta$=0.84/0.96 (2t, J=7.4 Hz, 3H, 9-H$_3$), 0.95/1.03 (2t, J=7.6, 3H, CH$_3$, 6-Et), 1.26–1.49 (m, 2H, 8-H$_2$), 1.78/1.79 (2br. s, 3H, 5-Me), 1.91/1.93 (2dd, J=1.6, 0.8 Hz, 3H, 1-H$_3$), 1.91–2.12 (m, 4H, C-7, CH$_2$, 6-Et), 6.12/6.14 (2dq, J=15.8, 1.6 Hz, 1H, 3-H), 6.76/6.77 (2dq, J=15.8, 7.0 Hz, 1H, 2E-H). -$^{13}$C-NMR (CDCl$_3$): $\delta$=12.33/13.03 (2q, C-9), 14.08/14.19 (2q, CH$_3$, 6-Et), 15.52/15.77 (2q, 5-Me), 18.19 (2q, C-1), 21.13/21.59 (2t, C-8), 23.91/26.34 (2t, CH$_2$, 6-Et), 32.44/35.23 (2t, C-7), 129.95/130.10 (2s, C-5), 132.17/132.21 (2d, C-3), 141.66/142.03 (2s, C-6), 145.04/145.15 (2d, C-2), 201.26/201.44 (2s, C-4). -MS (EI): m/e (%)=41 (80) [C$_3$H$_5$], 55 (38) [C$_4$H$_7$], 69 (64) [C$_4$H$_5$O], 123 (100) [M$^+$-C$_4$H$_9$], 137 (31) [M$^+$-C$_3$H$_7$], 151 (93) [M$^+$-C$_2$H$_5$], 165 (41) [M$^+$-CH$_3$], 180 (11) [M$^+$].

Example 7

(5Z)-2,5,6,7-Tetramethylocta-2,5-dien-4-one (7)

Odor: Fruity-rosy, reminiscent of dried fruits, weaker than compound 2, but more intensive than the corresponding (5E)-isomer [(5E)-7]. -IR (film): $\nu$=1612 cm$^{-1}$ ($\nu$C=C), 1667 ($\nu$C=O, unsat.), 1378 ($\delta$CH$_3$). -$^1$H-NMR (CDCl$_3$): $\delta$=0.96 (d, J=6.8 Hz, 6H, 7-Me$_2$), 1.58 (q, $^5$J=0.8 Hz, 3H, 6-Me), 1.75 (q, $^5$J=0.8 Hz, 3H, 5-Me), 1.91 (d, J=1.4 Hz, 3H, 2E-Me), 2.15 (d, J=1.1 Hz, 3H, 2Z-Me), 2.82 (sept, J =6.8 Hz, 1H, 7-H), 6.09 (s, 1H, 3-H). -NOESY ($^1$H/$^1$H): 3-H/8-H$_3$, 1-H/3-H, 3-H/5-Me, 5-Me/6-Me, 6-Me/8-H$_3$. -$^{13}$C-NMR (CDCl$_3$): $\delta$=11.78 (q, 5-Me), 15.39 (q, 6-Me), 20.47 (2q, C-1, 2-Me), 27.58/27.63 (2q, 7-Me$_2$), 31.78 (d, C-7), 125.00 (d, C-3), 132.08 (s, C-5), 141.14 (s, C-6), 154.37 (s, C-2), 199.88 (s, C-4). -MS (EI): m/e (%)=43 (26) [C$_3$H$_7$], 55 (52) [C$_4$H$_7$], 83 (59) [C$_5$H$_7$O], 123 (32) [M$^+$-C$_4$H$_9$], 137 (43) [M$^+$-C$_3$H$_7$], 150 (27) [M$^+$-2CH$_3$], 165 (100) [M$^+$-CH$_3$], 180 (20) [M$^+$].

Example 8

(2E,5E)-5,6,7,7-Tetramethylocta-2,5-dien-4-one (8)

Odor: Fruity, intensively reminiscent of apples, but also strongly reminiscent of dried fruits, having a somewhat celery- and jasmone-like side, and agrestic aspects. -IR (film): $\nu$=1653 cm$^{-1}$ ($\nu$C=O, unsat.), 972 ($\delta$C=C—H oop.), 1621 ($\nu$C=C), 1377 ($\delta$CH$_3$). -$^1$H-NMR (CDCl$_3$): $\delta$=1.21 (s, 9H, 7-Me$_3$), 1.57 (q, J=1.5 Hz, 3H, 6-Me, 5E), 1.88 (q, J=1.5 Hz, 3H, 5E-Me), 1.93 (dd, J=7.0, 1.6 Hz, 3H, 1-H$_3$), 6.04 (dq, J=15.7, 1.6 Hz, 1H, 3-H, 2E), 6.74 (dq, J=15.7, 6.8 Hz, 1H, 2E-H). —NOESY ($^1$H/$^1$H): 5-Me/7-Me$_3$, 6-Me/7-Me$_3$. -$^{13}$C-NMR (CDCl$_3$): $\delta$=17.80 (q, 5-Me), 18.29 (q, C-1), 19.11 (q, 6-Me), 29.82 (3q, 7-Me$_3$), 35.88 (s, C-7), 130.43 (s, C-5), 131.92 (d, C-3), 140.35 (s, C-6), 145.73 (d, C-2), 203.15 (s, C-4). -MS (EI): m/e (%)=41 (81) [C$_3$H$_5$], 57 (76) [C$_4$H$_9$], 69 (65) [C$_5$H$_9$], 109 (38) [M$^+$-C$_5$H$_{11}$], 124 (30) [M$^+$-C$_4$H$_8$], 137 (24) [M$^+$-C$_3$H$_7$], 150 (9) [M$^+$-2CH$_3$], 165 (100) [M$^+$-CH$_3$], 180 (10) [M$^+$].

Example 9

(2E,5Z)-6-Ethyl-5,7-dimethylocta-2,5-dien-4-one (9)

Odor: Fruity-rosy, reminiscent of raspberries, and dried fruits, more intensive, more diffusive, and more agrestic than the corresponding (5E)-isomer [(5E)-9] which, however, smells more like fresh apples. -IR (film): $\nu$=1651 cm$^{-1}$ ($\nu$C=O, unsat.), 972 ($\delta$C=C—H oop.), 1621 ($\nu$C=C), 1376 ($\delta$CH$_3$). -$^1$H-NMR (CDCl$_3$): $\delta$=0.94 (d, J=6.8 Hz, 6H, 7-Me$_2$), 1.06 (t, J=7.6 Hz, 3H, CH$_3$, 6-Et), 1.77 (s, 3H, 5-Me), 1.93 (dd, J=6.8, 1.6 Hz, 3H, 1-H$_3$), 2.07 (q, J=7.6 Hz, 2H, CH$_2$, 6-Et), 2.54 (sept, J=6.8 Hz, 1H, 7-H), 6.11 (dq, J=15.7, 1.6 Hz, 1H, 3-H, hence 2E), 6.77 (dq, J=15.7, 6.8 Hz, 1H, 2-H, hence 2E). -NOESY ($^1$H/$^1$H): 5-Me/CH$_2$CH$_3$. -$^{13}$C-NMR (CDCl$_3$): $\delta$=14.08 (q, 5-Me), 15.64 (q, CH$_3$, 6-Et), 18.15 (q, C-1), 19.32 (t, CH$_2$, 6-Et), 20.82 (2q, 7-Me$_2$), 32.94 (d, C-7), 129.41 (s, C-5), 132.55 (d, C-3), 145.37 (d, C-2), 145.55 (s, C-6), 202.26 (s, C-4). -MS (EI): m/e (%)=41 (80) [C$_3$H$_5$], 55 (29) [C$_4$H$_7$], 69 (61) [C$_5$H$_9$], 81 (17)/95 (17)/109 (24)/123 (40)/137 (76)/151 (36)/165 (100) [M$^+$-C$_n$H$_{2n+1}$], 180 (14) [M$^+$].

Example 10

Floral-Fruity-Green Female Fragrance Containing Compound 1

The following components were combined as indicated to form the fragrance:

| No. | Compound/Constituent | Parts by weight in % |
|---|---|---|
| 1. | Adoxal | 3 |
| 2. | Ambrofix, 10% in BB | 15 |
| 3. | Benzyl acetate, extra | 6 |
| 4. | Bergamot oil | 80 |
| 5. | Calone 1951 | 4 |
| 6. | Cedryl methyl ether | 5 |
| 7. | Citronellyl acetate | 15 |
| 8. | Citronellol, extra | 35 |
| 9. | Dimetol | 2 |
| 10. | DPG (dipropylene glycol) | 94 |
| 11. | Estragol | 1 |
| 12. | Ethyllinalool | 35 |
| 13. | Ethyl-3-methyl-3-phenylglycidate (strawberry aldehyde) | 1 |
| 14. | Eugenol, very pure | 3 |
| 15. | Floralozone [3-(4-ethylphenyl)-2,2-dimethylpropanal], 10% in DPG | 4 |
| 16. | Floropal (2,4,6-trimethyl-4-phenyl-1,3-dioxane) | 3 |
| 17. | Galaxolide 50 PHT (4,6,6,7,8,8,-hexamethyl-1,3,4,6,7,8-hexahydrocyclopenta[g]benzopyran) | 140 |
| 18. | Gardenol (1-phenylethyl acetate) | 30 |
| 19. | Hedione (methyl dihydrojasmonate) | 120 |
| 20. | cis-3-Hexenyl acetate, 10% in DPG | 17 |
| 21. | cis-3-Hexenyl salicylate | 9 |
| 22. | Iso E Super | 60 |
| 23. | Isoraldein 70 (methylionone) | 35 |
| 24. | Lavender oil, French | 7 |
| 25. | Lilial [2-methyl-3-(4-tert-butylphenyl)propanal] | 90 |
| 26. | Melonal (2,6-dimethyl-5-hepten-1-al), 10% in DPG | 12 |
| 27. | 3-(4-Methoxyphenyl)-2-methylpropanal | 6 |
| 28. | 1-Phenyl-2-methylprop-2-yl acetate | 9 |
| 29. | Sandalore [5-(2,2,3-trimethyl-3-cyclopenten-1-yl)-3-methylpentan-2-ol] | 15 |
| 30. | Tagette oil, extra | 3 |
| 31. | Terpineol | 10 |
| 32. | Tropional [2-methyl-3-(3,4-methylenedioxyphenyl) propanal] | 48 |
| 33. | Viridine (2-phenylacetaldehyde dimethyl acetal) | 1 |
| 34. | Ylang-ylang oil | 2 |
| 35. | Lemon oil, Italian | 30 |
| 36. | Compound 1, 10% in DPG | 50 |
| | | 1000 |

This composition gives a feminine, floral-aquatic perfume with a hesperidic-green top note of bergamot, citrus, and lavender notes, rosy, lily-of-the-valley, and watermelon-accentuated middle notes, and fruity-musklike-woody base note.

Compound 1 combines harmoniously with the rose accord and emphasizes it, like the fruity aspects of this creation. Moreover, it also integrates harmoniously the lavender-like facets in the initial odor. Compared with damascones and their analogs, the hesperidic elements are much more strongly emphasized and, moreover, compound 1 gives the scent a very much greater diffusivity than would be the case if damascones were used.

Example 11

Perfume Composition Containing Compound 1 for a Cream Soap

The following components were combined as indicated to form the perfume:

| No. | Compound/Constituent | Parts by weight in 1/1120 |
|---|---|---|
| 1. | Benzyl acetate, extra | 10 |
| 2. | Benzyl salicylate | 4 |
| 3. | Citronellol, extra | 200 |
| 4. | Dimethyl sulfide, 1% in triethyl citrate | 0.1 |
| 5. | Ethylvanillin | 0.4 |
| 6. | Eugenol, pure | 2.5 |
| 7. | Geraniol, extra | 110 |
| 8. | Geranium, Bourbon RGV | 20 |
| 9. | Geranyl acetate, pure | 10 |
| 10. | cis-3-Hexenol | 1 |
| 11. | Irisantheme [3-methyl-4-(2,6,6-trimethyl-2-cyclohexen-1-yl)-3-buten-2-one] | 60 |
| 12. | Isopulegol | 2 |
| 13. | Camomile oil, Roman | 1 |
| 14. | Koavone | 3 |
| 15. | Laurylaldehyde | 1 |
| 16. | Nerol | 90 |
| 17. | Nonanal | 1.5 |
| 18. | Methyl 2-nonynoate | 0.5 |
| 19. | 2-Phenylacetaldehyde, 85% strength in 2-phenylethyl alcohol | 2 |
| 20. | 2-Phenylacetic acid, pure, crystalline | 0.5 |
| 21. | 2-Phenylethyl alcohol | 420 |
| 22. | Phenethyl phenylacetate | 0.5 |
| 23. | 1-Phenyl-2-methyl-2-propanyl acetate | 6 |
| 24. | Rosacetol (alpha-trichloromethylbenzyl acetate) | 6 |
| 25. | Cinnamon rose, RHS MEF | 2 |
| 26. | Rose oxide | 1 |
| 27. | Cinnamyl alcohol, synthetic | 15 |
| 28. | Compound 1, 1% in DPG | 150 |

-continued

| No. | Compound/Constituent | Parts by weight in 1/1120 |
|-----|---------------------|---------------------------|
|     |                     | 1120                      |

This composition gives a fruity-rosy perfume oil, reminiscent of the typical scent of the Bulgarian rose.

Compound 1 represents a scent cornerstone in this markedly rosy composition. It gives the creation a very much more natural character than the damascones which, in direct contrast, shifts the overall impression more in the direction of plums, wood, and wine notes. Moreover, compound 1 introduces more apple-like, green aspects to the composition and thus better brings out the mild cleansing, caring product character of the cream soap.

The invention being thus described, it will be obvious that the same may be varied in many ways. Such variations are not to be regarded as a departure from the spirit and scope of the invention and all such modifications are intended to be included within the scope of the following claims.

What is claimed is:

1. A compound of the general formula I

I wherein
$R^1$ and $R^2$ independently are $CH_2$, $CH_3$, $CHCH_3$, or $CH_2CH_3$;
$R^3$=H, $CH_3$, $CH_2CH_3$;
$R^4$, $R^5$, $R^6$, and $R^7$ are H or $CH_3$; with the proviso that $R^4$, $R^5$, $R^6$, $R^7$ are not all hydrogen, and where the dashed line represents a single bond, or one of the bonds $R^1$-C5, C5-C6 or C6-$R^2$ represents a double bond and when $R^3$ and $R^4$ are hydrogen, at least one of $R^5$ or $R^6$ is $CH_3$.

2. A compound according to claim 1 having an (E)-configured double bond between C-5 and C-6.

3. A compound according to claim 1 wherein $R^4$ is $CH_3$.

4. A compound according to claim 1 having an (E)-configured double bond between C-5 and C-6 and wherein $R^4$ is $CH_3$.

5. A compound according to claim 1 selected from the group (2E,5Z)-5,6,7-trimethylocta-2,5-dien-4-one, (2E)-5,6,7-trimethyloct-2-en-4-one, (2E,5Z)-5,6,7-trimethylnona-2,5-dien-4-one, (2E,5E/Z)-6-ethyl-5,7-dimethylnona-2,5-dien-4-one, (2E,5E/Z)-6-ethyl-5-methylnona-2,5-dien-4-one, (2E,5Z)-2,5,6,7-tetramethylocta-2,5-dien-4-one, (2E,5E)-5,6,7,7-tetramethylocta-2,5-dien-4-one, (2E,5Z)-6-ethyl-5,7-dimethylocta-2,5-dien-4-one and all their double-bond isomers, and (2E,5E/Z)-5,6,7-trimethylocta-2,5-dien-4-one.

6. A fragrance or aroma composition comprising a compound according to claim 1.

7. A fragrance or aroma composition comprising a compound according to claim 2.

8. A fragrance or aroma composition comprising a compound according to claim 3.

9. A fragrance or aroma composition comprising a compound according to claim 4.

10. A process for preparing a fragrance, a flavor, or an aroma composition comprising combining with a base material a compound of the general formula I:

I wherein
$R^1$ and $R^2$ independently are $CH_2$, $CH_3$, $CHCH_3$, or $CH_2CH_3$;
$R^3$=H, $CH_3$, $CH_2CH_3$;
$R^4$, $R^5$, $R^6$, and $R^7$ are H or $C_3$; with the proviso that $R^4$, $R^5$, $R^6$, $R^7$ are not all hydrogen, and where the dashed line represents a single bond, or one of the bonds $R^1$-C5, C5-C6 or C6-$R^2$ represents a double bond and when $R^3$ and $R^4$ are hydrogen, at least one of $R^5$ or $R^6$ is $CH_3$.

11. A process according to claim 10 having an (E)-configured double bond between C-5 and C-5.

12. A process according to claim 10 wherein $R^4$ is $CH_3$.

13. A process according to claim 10 having an (E)-configured double bond between C-5 and C-6 and wherein $R^4$ is $CH_3$.

14. A process according to claim 10 wherein the compound of general formula I is selected from the group (2E,5Z)-5,6,7-trimethylocta-2,5-dien-4-one, (2E)-5,6,7-trimethyloct-2-en-4-one, (2E,5Z)-5,6,7-trimethylnona-2,5-dien-4-one, (2E,5E/Z)-6-ethyl-5,7-dimethylnona-2,5-dien-4-one, (2E, 5E/Z)-6-ethyl-5-methylnona-2,5-dien-4-one, (2E,5Z)-2,5,6,7-tetramethylocta-2,5-dien-4-one, (2E,5E)-5,6,7,7-tetramethylocta-2,5-dien-4-one, (2E,5Z)-6-ethyl-5,7-dimethylocta-2,5-dien-4-one and all their double-bond isomers, and (2E,5E/Z)-5,6,7-trimethylocta-2,5-dien-4-one.

15. A process for delivering a fragrance, a flavor, or aroma to a substrate comprising: contacting a substrate with a fragrance, flavour, or aroma composition comprising a base material and a compound of formula I:

I wherein
$R^1$ and $R^2$ independently are $CH_2$, $CH_3$, $CHCH_3$, or $CH_2CH_3$;
$R^3$=H, $CH_3$, $CH_2CH_3$;
$R^4$, $R^5$, $R^6$ and $R^7$ are H or $CH_3$; with the proviso that $R^4$, $R^5$, $R^6$, $R^7$ are not all hydrogen, and where the dashed line represents a single bond, or one of the bonds $R^1$-C5, C5-C6 or C6-$R^2$ represents a double bond and when $R^3$ and $R^4$ are hydrogen, at least one of $R^5$ or $R^6$ is $CH_3$.

16. A process according to claim 15 wherein the substrate is selected from the group consisting of skin, hair, a fabric, and a hard surface.

17. A process according to claim 15 wherein the compound of formula I is selected from the group (2E,5Z)-5,6,7-trimethylocta-2,5-dien-4-one, (2E)-5,6.7-trimethyloct-2-en-4-one, (2E,5Z)-5,6,7-trimethylnona-2,5-dien-4-one, (2E,5E/Z)-6-ethyl-5,7-dimethylnona-2,5-dien-4-one, (2E,5E/Z)-6-ethyl-5-methylnona-2,5-dien-4-one, (2E,5Z)-Z,2,5,6,7-tetramethylocta-2,5-dien-4-one, (2E,5E)-5,6,7,7-tetramethylocta-2,5-dien-4-one, (2E,5Z)-6-ethyl-5,7-dimethylocta-2,5-dien-4-one and all their double-bond isomers, and (2E,5E/Z)-5,6,7-trimethylocta-2,5-dien-4-one.

18. A fragrance or aroma composition consisting essentially of a compound of formula I:

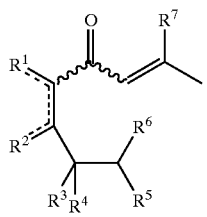

I wherein $R^1$ and $R^2$ independently are $CH_2$, $CH_3$, $CHCH_3$, or $CH_2CH_3$;

$R^3$=H, $CH_3$, $CH_2CH_3$;

$R^4$, $R^5$, $R^6$, and $R^7$ are H or $CH_3$; with the proviso that $R^4$, $R^5$, $R^6$, $R^7$ are not all hydrogen, and where the dashed line represents a single bond, or one of the bonds $R^1$-C5, C5-C6 or C6-$R^2$ represents a double bond and when $R^3$ and $R^4$ are hydrogen, at least one of $R^5$ or $R^6$ is $CH_3$; and a flavoring or aroma effective carrier or excipient.

19. A compound according to claim 5 selected from the group (2E,5E/Z)-6-ethyl-5-methylnona-2,5-dien-4-one and (2E,5Z)-6-ethyl-5,7-dimethylocta-2,5-dien-4-one.

* * * * *